(12) United States Patent
Lee et al.

(10) Patent No.: US 7,368,514 B2
(45) Date of Patent: May 6, 2008

(54) SILOXANE MONOMER CONTAINING TRIFLUOROVINYLETHER GROUP AND SOL-GEL HYBRID POLYMER PREPARED BY USING THE SAME

(75) Inventors: Jae-Suk Lee, Gwangju (KR); Kwan-Soo Lee, Gwangju (KR); Ho-Suk Song, Gwangju (KR); Jae-Pil Kim, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 265 days.

(21) Appl. No.: 10/881,557

(22) Filed: Jun. 30, 2004

(65) Prior Publication Data
US 2005/0107561 A1 May 19, 2005

(30) Foreign Application Priority Data
Nov. 18, 2003 (KR) .................... 10-2003-0081489

(51) Int. Cl.
*C07F 7/18* (2006.01)
(52) U.S. Cl. .................. 526/247; 526/279; 556/485; 522/88
(58) Field of Classification Search ........... 556/485; 526/247, 279; 522/99
See application file for complete search history.

(56) References Cited

U.S. PATENT DOCUMENTS

| 2,884,434 | A | * | 4/1959 | Smith | 556/434 |
| 2,983,711 | A | * | 5/1961 | Gordon | 528/40 |
| 5,246,782 | A | * | 9/1993 | Kennedy et al. | 428/421 |
| 5,948,929 | A | * | 9/1999 | Mileshkevich | 556/448 |
| 6,803,476 | B2 | * | 10/2004 | Rantala et al. | 556/477 |
| 6,953,653 | B2 | * | 10/2005 | Smith et al. | 430/321 |
| 7,062,145 | B2 | * | 6/2006 | Rantala et al. | 385/145 |

OTHER PUBLICATIONS

Ma, Hong et al.; "A Novel Class of High-Performance Perfluorocyclobutane-Containing Polymers for Second-Order Nonlinear Optics", *Chem. Mater 2000*, 12;pp. 1187-1189.

Liu, Sen et al.; "Triarylamine-Containing Poly(perfluorocyclobutane) as Hole-Transporting Material for Polymer Light-Emitting Diodes", *Macromolecules 2000*, 33; pp. 3514-3517.

Kim, Jae-Pil et al.; "Hydrolysis and condensation of fluorine containing organosilicon", *Optical Materials* 21 (2002); pp. 445-450.

* cited by examiner

*Primary Examiner*—Margaret G. Moore
(74) *Attorney, Agent, or Firm*—Frommer Lawrence & Haug LLP; Ronald R. Santucci

(57) ABSTRACT

The present invention relates to a siloxane monomer containing a trifluorovinylether group and a sol-gel hybrid polymer prepared using the monomer, more particularly to siloxane monomer with novel structure prepared by reacting alkoxychlorosilane with a Grignard reagent containing a trifluorovinylether ($-OC_2F_3$) group, a method of preparing the same and a sol-gel hybrid polymer containing a perfluorocyclobutane (PFCB) group prepared from sol-gel reaction using said siloxane monomer containing a trifluorovinylether group.

4 Claims, 11 Drawing Sheets

US 7,368,514 B2

SILOXANE MONOMER CONTAINING TRIFLUOROVINYLETHER GROUP AND SOL-GEL HYBRID POLYMER PREPARED BY USING THE SAME

This application claims priority benefits of Korean Patent Application No. KR 2003-0081489 filed Nov. 18, 2003.

BACKGROUND OF THE INVENTION

1. Field of the Invention

The present invention relates to a siloxane monomer containing a trifluorovinylether group and a sol-gel hybrid polymer prepared using the monomer, more particularly to siloxane monomer with novel structure prepared by reacting alkoxychlorosilane with a Grignard reagent containing a trifluorovinylether ($-OC_2F_3$) group, a method of preparing the same and a sol-gel hybrid polymer containing a perfluorocyclobutane (PFCB) group prepared from sol-gel reaction using the siloxane monomer containing a trifluorovinylether group.

2. Description of Related Art

Fluorine (F)-containing polymers are widely used for such materials as thermoplastic polymers, membranes and elastomers because of good thermal stability, low dielectricity and superior hygroscopy, flame resistance and chemical resistance. Especially, they are used to manufacture optical waveguide devices. However, it is difficult to make fluorine-containing polymers into electronic devices, because they do not have good adhesivity to silicon wafers.

On the other hand, siloxane-containing sol-gel polymers are known to have good thermal stability and adhesivity to silicon wafers.

Currently, development of fluorine-containing polymers having superior adhesivity and thermal stability is highly required.

SUMMARY OF THE INVENTION

The present inventors have tried to solve the adhesivity and thermal stability problem of fluorine-containing polymers for years. In doing so, they prepared a novel monomer containing a trifluorovinylether ($-OC_2F_3$) group, fluorine (F) and silicon (Si) from Grignard reaction of a Grignard reagent containing a trifluorovinylether ($-OC_2F_3$) group, which is capable of forming perfluorocyclobutane (PFCB) by sol-gel reaction, with alkoxychlorosilane. They found out that a sol-gel hybrid polymer prepared using the novel monomer has significantly improved adhesivity and thermal stability due to introduction of siloxane group.

Thus, it is an object of the present invention to provide a siloxane monomer containing a trifluorovinylether ($-OC_2F_3$) group, fluorine (F) and silicon (Si), and a method of preparing the same.

It is another object of the present invention to provide a sol-gel hybrid polymer containing perfluorocyclobutane (PFCB), which is prepared by using the novel monomer, and a method of preparing the same.

It is still another object of the present invention to provide a sol-gel film prepared by using the sol-gel hybrid polymer containing perfluorocyclobutane (PFCB).

DETAILED DESCRIPTION OF THE PREFERRED EMBODIMENTS

Figure 1:
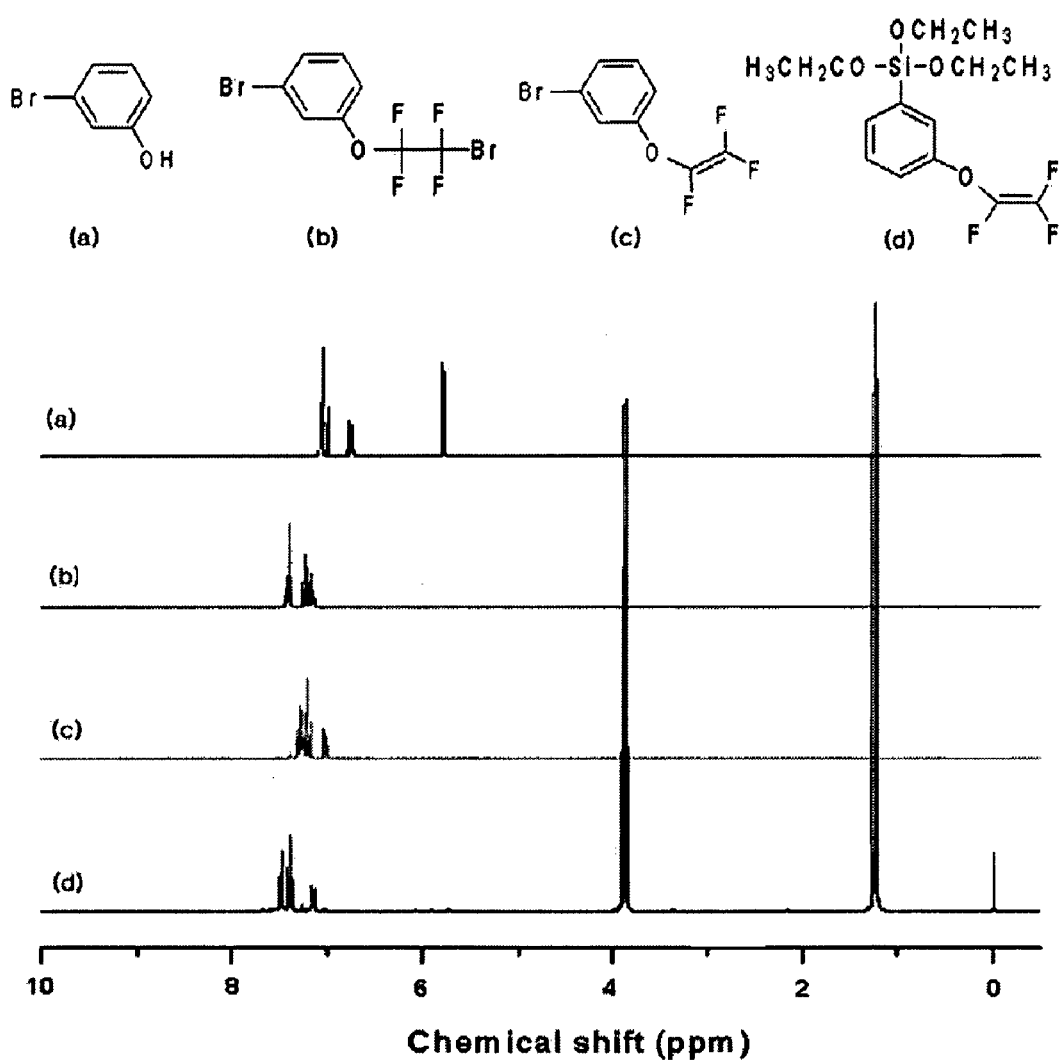
FIG. 1 shows $^1$H-NMR spectrums of 3-bromophenol, 3-(2-bromotetrafluoroethoxy)bromobenzene, 3-[(trifluorovinyl)oxy]bromobenzene and [3-[(trifluorovinyl)oxy]phenyl]triethoxysilane (PFCBSI).

The present invention is characterized by siloxane monomer represented by the following Chemical Formula 1:

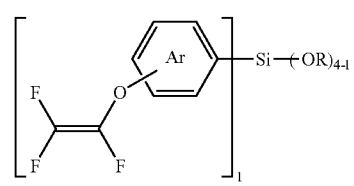

(1)

wherein

R is a hydrogen atom or a $C_1$ to $C_6$ alkyl group;

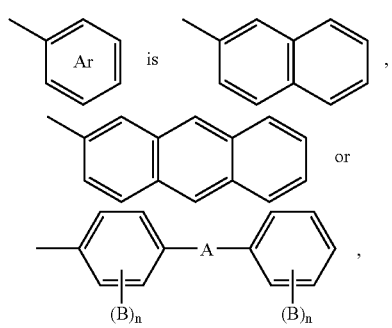

wherein trifluorovinylether ($-OC_2F_3$) group can be substituted at o-, m- or p-position;

-A- is a bonding,

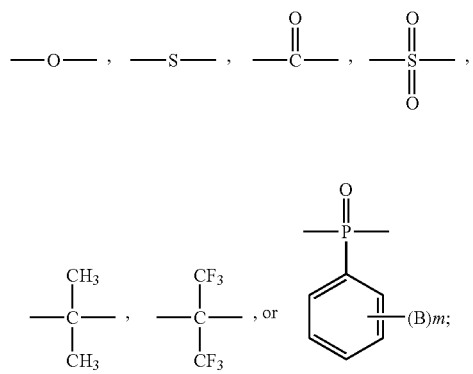

B is a hydrogen atom, a fluorine atom, a $C_1$ to $C_6$ alkyl group or a $C_1$ to $C_6$ fluoroalkyl group;

n and m are respectively the number of substituents B, wherein n is an integer of 1 to 4 and m is an integer of 1 to 5; and l is an integer of 1 to 4.

The present invention also relates to a sol-gel hybrid polymer represented by Chemical Formula 2 below, which is prepared from sol-gel reaction of the siloxane monomer represented by Chemical Formula 1:

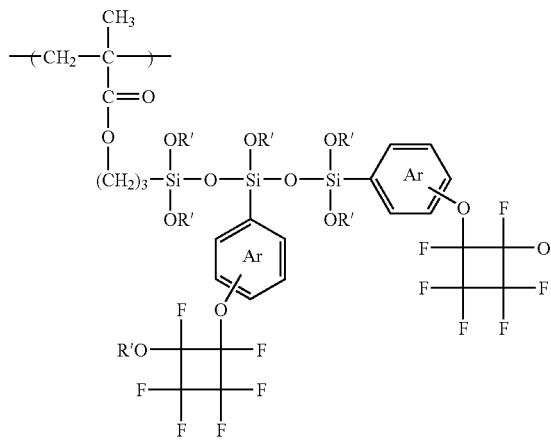

(2)

wherein

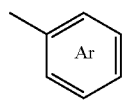

is the same as defined above; and

R' is a hydrogen atom or a $C_1$ to $C_6$ alkyl group,

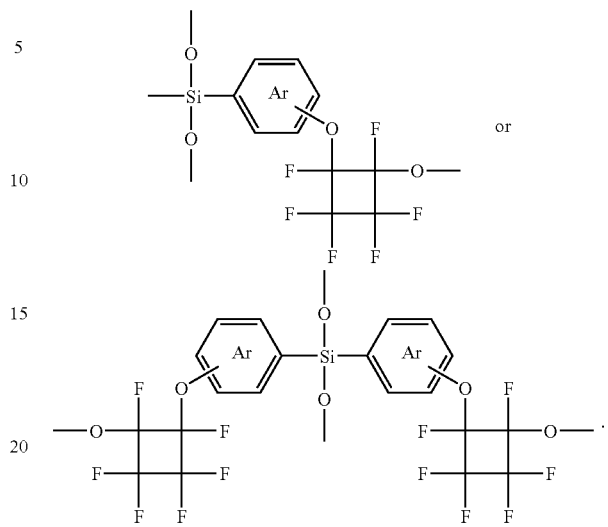

Hereinafter, the present invention is described in more detail.

The novel siloxane monomer of the present invention, which is represented by Chemical Formula 1, has a trifluorovinylether ($-OC_2F_3$) group, fluorine (F) and silicon (Si). The trifluorovinylether ($-OC_2F_3$) group present in the monomer of the present invention can form perfluorocyclobutane (PFCB) by sol-gel reaction to give linear or crosslinked amorphous film. It reacts readily by heat in the absence of special catalyst or initiator to give a sol-gel polymer containing fluorine (F). The sol-gel polymer prepared using the monomer of the present invention is amorphous because it contains perfluorocyclobutane (PFCB). It has low birefringence and superior adhesivity, while maintaining inherent thermal stability of fluorine-containing polymer. Therefore, it is useful for information technology devices.

The process of preparing the novel monomer of the present invention represented by Chemical Formula 1 is as follows:

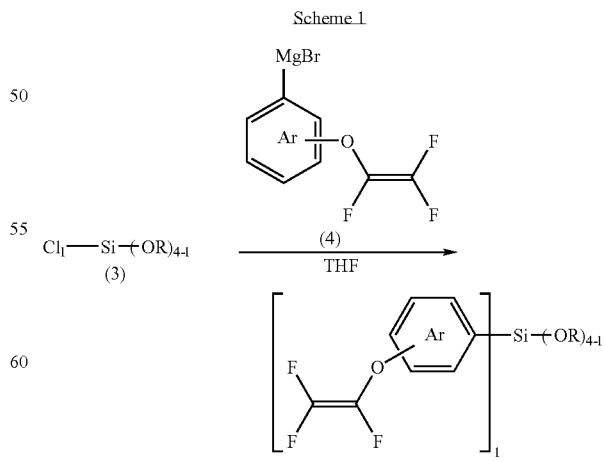

wherein R is a hydrogen atom or a $C_1$ to $C_6$ alkyl group and l is an integer of 1 to 4.

In the monomer preparation by Grignard reaction according to Scheme 1, the alkoxychlorosilane, which is represented by Chemical Formula 3, and the Grignard reagent containing a trifluorovinylether (—$OC_2F_3$) group, which is represented by Chemical Formula 4, are reacted at a temperature ranging from −100 to 100° C. for 10 hours to overnight while stirring to prepare the siloxane monomer represented by Chemical Formula 1. For the reaction solvent, any common organic solvent including tetrahydrofuran (THF) may be used. After the Grignard reaction is completed, the reaction solution is vacuum-distilled and purified by the conventional method, e.g., by chromatography, to obtain the target monomer of the present invention.

The Grignard reagent represented by Chemical Formula 4 can be easily prepared by the conventional method using bromobenzene containing a trifluorovinylether (—$OC_2F_3$) group and magnesium.

The process of preparing a sol-gel hybrid polymer using the siloxane monomer of the present invention is as follows:

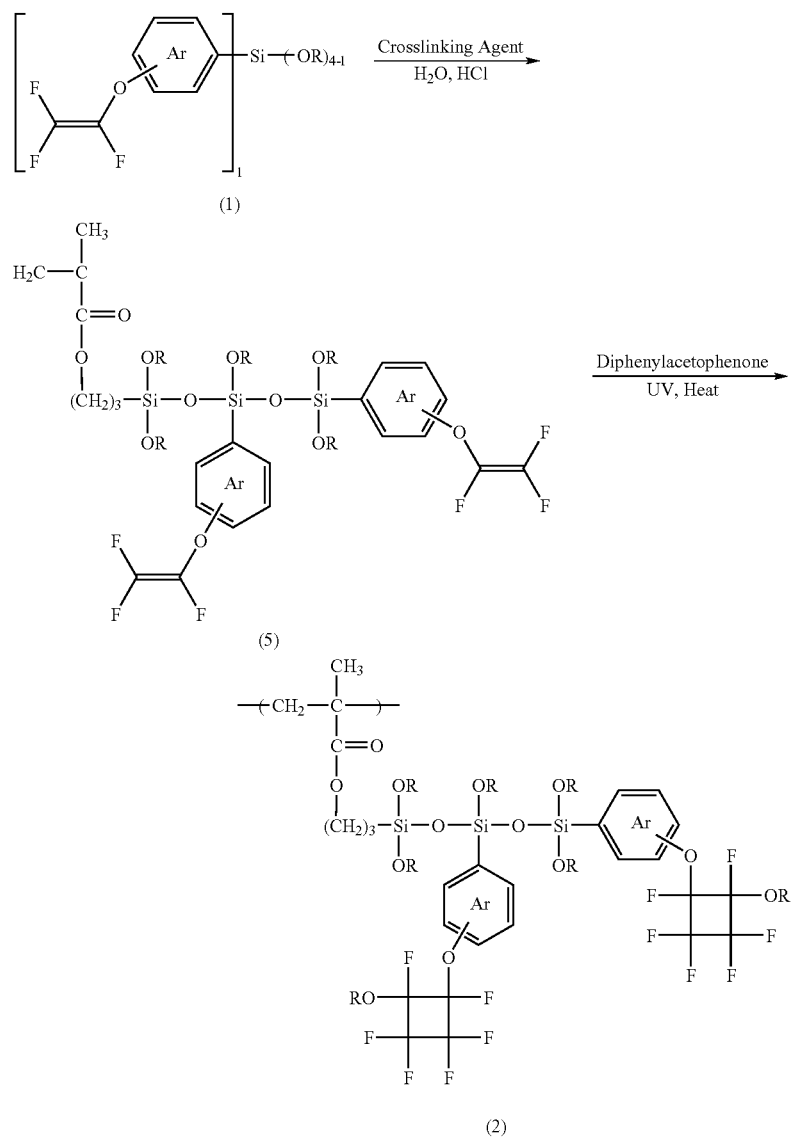

wherein R and R' are the same as defined above.

First, the siloxane monomer represented by Chemical Formula 1 is sol-gel reacted in the presence of a crosslinking agent, water and an acid to prepare a sol-gel monomer containing a trifluorovinylether (—$OC_2F_3$) group, which is represented by Chemical Formula 5. During the sol-gel reaction, the proportion of water and acid is important. Preferably, water is used in a molar ratio of 1:2 to 4 for the siloxane monomer. And, the acid is used in a molar ratio of 1:1 to 3 for the siloxane monomer. If too little water is used, unreacted monomers remain due to incomplete hydrolysis. In contrast, if too much water is used, it takes time for the siloxane monomers to react, thereby increasing the reaction time. And, if too much or too little acid is used, the sol stability decreases and the gelation time becomes short. For the above acid, inorganic acids, such as hydrochloric acid, sulfuric acid and nitric acid may be used. During the sol-gel reaction, a crosslinking agent is added to prevent cracking of the sol-gel film. For the above crosslinking agent, triethoxyvinylsilane, 4-methoxydimethylsilylstyrene, 4-ethoxydimethylsilylstyrene, 4-isopropoxydimethylsilylstyrene, 4-t-butoxydimethylsilylstyrene, 4-diethoxymethylsilylstyrene or 4-triethoxysilylstyrene, 3-(triethoxysilyl)propylmethacrylate may be used. Preferably, the crosslinking agent is used in a molar ratio of 3:7 to 7:3 for the siloxane monomer.

Then, the obtained sol-gel monomer is polymerized using 2,2-dimethoxy-2-phenylacetophenone as photoinitiator and heated to 100 to 200° C. to prepare a sol-gel hybrid polymer containing PFCB and silicon.

The resultant polymer, which is represented by Chemical Formula 2, contains perfluorocyclobutane (PFCB) and shows heat stability and dielectricity comparable to or better than those of the conventional fluorine-containing polymers. And, it shows significantly improved adhesivity and thermal stability because of introduction of the siloxane group.

Hereinafter, the present invention is described in more detail through Examples. However, the following Examples are only for the understanding of the present invention, and the present invention is not limited by the following Examples.

EXAMPLES

Example 1

Preparation of [3-[(trifluorovinyl)oxy]phenyl]triethoxysilane (PFCBSI)

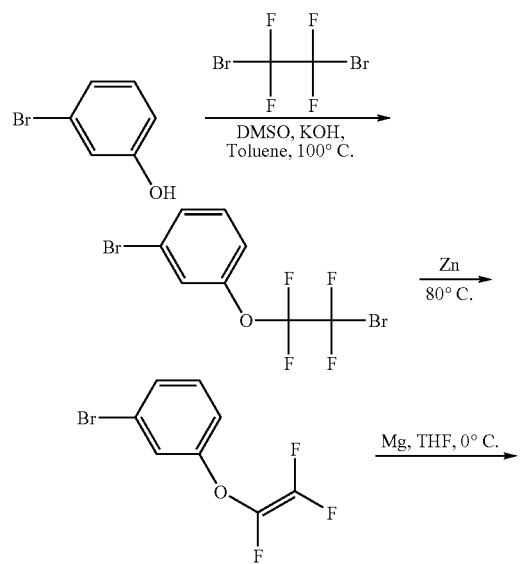

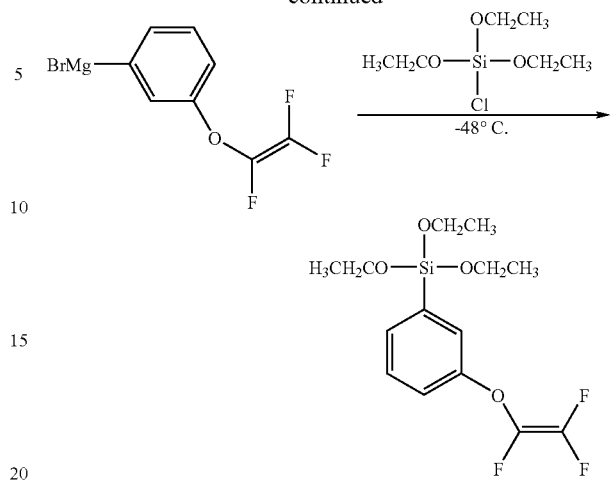

(1) Preparation of 3-(2-bromotetrafluoroethoxy)bromobenzene 3-bromophenol (0.582 mol), potassium hydroxide (0.582 mol), methyl sulfoxide (3.2 L) and xylene (0.08 L) were put in a 2-bulb flask equipped with a Dean-Stark azeotropic distillation unit, which has been purged with nitrogen. The reactor was heated to 100° C. and reaction was performed for 48 hours to remove water. The reactor was cooled to 30° C. and 1,2-dibromotetrafluoroethane (0.640 mol) was slowly dropped for 4 hours maintaining the reactor temperature below 30° C. The reaction solution was mixed at 22° C. for 12 hours, and then reaction was performed at 35° C. for 10 hours. After the reaction was completed, the reaction solution was extracted with methylene chloride diluted in water. The obtained product was washed with water for three times and dehydrated with magnesium sulfate. Methylene chloride was removed from the filtrate using a vacuum evaporator. From vacuum distillation, 3-(2-bromotetrafluoroethoxy)bromobenzene was obtained as clear liquid (boiling point: 107 to 110° C.). The yield was 72%.

Figure 2:
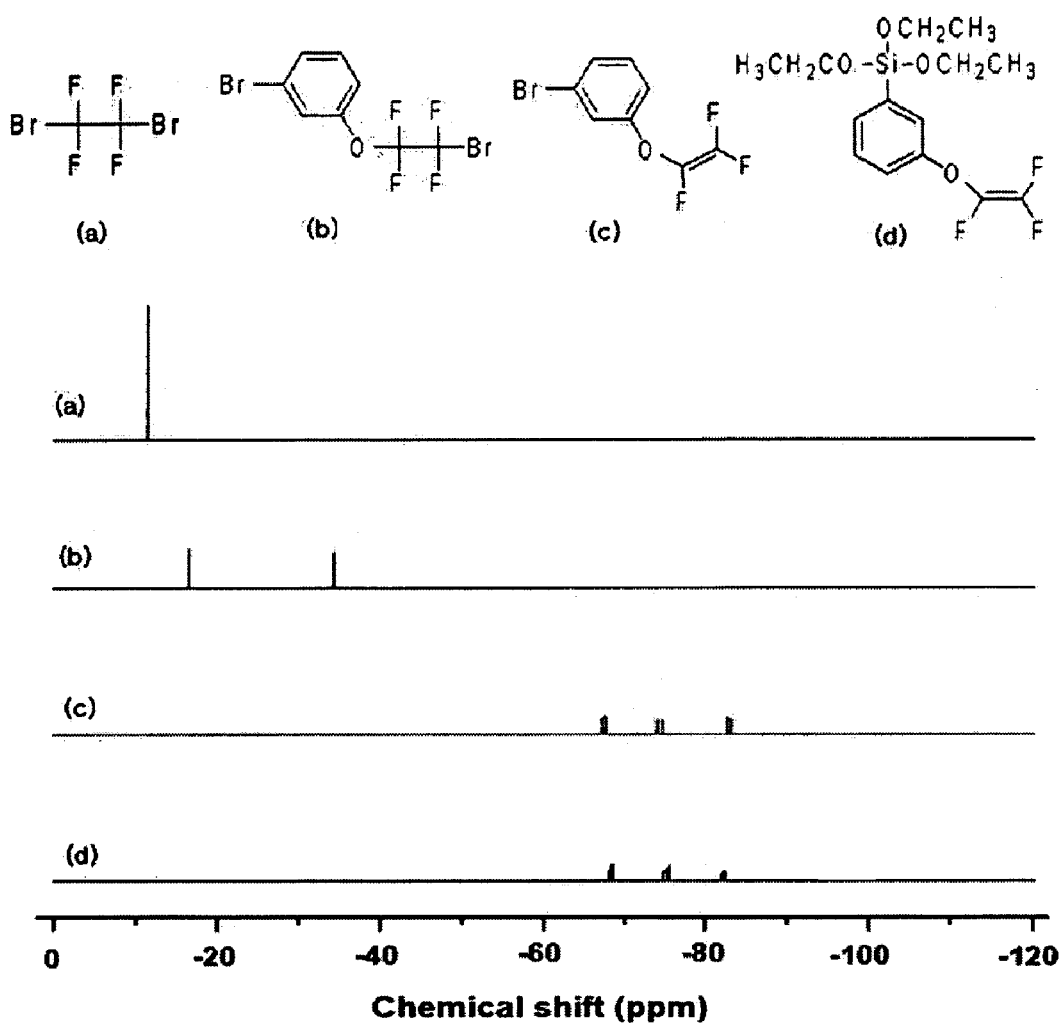
FIG. 2 shows $^{19}$F-NMR spectrums of 1,2-dibromotetrafluoroethane, 3-(2-bromotetrafluoroethoxy)bromobenzene, 3-[(trifluorovinyl)oxy]bromobenzene and [3-[(trifluorovinyl)oxy]phenyl]triethoxysilane (PFCBSI).

$^1$H-NMR and $^{19}$F-NMR spectrums of the obtained 3-(2-bromotetrafluoroethoxy)bromobenzene are shown in FIG. 1 and FIG. 2, respectively. As seen in the $^1$H-NMR spectrum of FIG. 1, the hydrogen peak of the hydroxy group (5.79 ppm), which has been present in (a), is not seen in (b), which confirms preparation of the target product. In the $^{19}$F-NMR spectrum of FIG. 2, different peaks are seen in (a) [−11.62 ppm] and (b) [−16.71 and −34.55 ppm], which confirms presence of two different fluorines. From the $^1$H-NMR and $^{19}$F-NMR spectrums, preparation of 3-(2-bromotetrafluoroethoxy)bromobenzene was confirmed.

(2) Preparation of 3-[(trifluorovinyl)oxy]bromobenzene

Acetonitrile (3.5 L) and zinc (Zn) (0.462 mol) were put in a 2-bulb flask and mixed at 80° C. Then, 3-(2-bromotetrafluoroethoxy)bromobenzene prepared in (1) was slowly dropped for 3 hours. The reaction mixture was refluxed for 10 hours and then evaporated. The unpurified product was extracted with hexane. Hexane remaining in the filtrate was removed using a vacuum evaporator to obtain 3-[(trifluorovinyl)oxy]bromobenzene, which is in liquid state at room temperature (yield: 79.4%).

$^1$H-NMR and $^{19}$F-NMR spectrums of the obtained 3-[(trifluorovinyl)oxy]bromobenzene are shown in FIG. 1 and FIG. 2, respectively. As seen in the $^1$H-NMR spectrum of FIG. 1, all peaks of (c) shifted toward low magnetic filed in (b), which confirms presence of double bonding. The three peaks in the $^{19}$F-NMR spectrum of FIG. 2(c) at −67.52, −74.35 and −82.97 ppm are due to the double bond. From the $^1$H-NMR and $^{19}$F-NMR spectrum, preparation of 3-[(trifluorovinyl)oxy]bromobenzene was confirmed.

(3) Preparation of [3-[(trifluorovinyl)oxy]phenyl]triethoxysilane (PFCBSI)

Magnesium (0.12 mol) and tetrahydrofuran were put in a 2-bulb flask purged with nitrogen. Then, 3-[(trifluorovinyl)oxy]bromobenzene prepared in (2) was dropped very slowly maintaining the reactor temperature at 0° C. The reactor was put in an ice bath to prevent the temperature from rising rapidly. After adding 3-[(trifluorovinyl)oxy]bromobenzene, the reactor was heated to room temperature, and reaction was performed for 2 hours. Then, triethoxychlorosilane (0.95 mol) was dropped keeping the reactor temperature at −48° C. with a constant temperature bath filled with dry ice and acetonitrile. The reaction mixture was mixed at room temperature for 24 hours. After the reaction was completed, excess heptane was added to remove the obtained salt and unreacted magnesium. The filtrate was removed by filtering with filter paper. Heptane remaining in the filtrate was removed using a vacuum evaporator and vacuum-distilled to obtain [3-[(trifluorovinyl)oxy]phenyl]triethoxysilane (PFCBSI) (yield: 80%).

$^1$H-NMR and $^{19}$F-NMR spectrums of the obtained [3-[(trifluorovinyl)oxy]phenyl]triethoxysilane are shown in FIG. 1 and FIG. 2, respectively. Ethyl Hydrogen peaks of ethyl group, which is present in the target monomer, are shown at 3.88 and 1.25 ppm of the $^1$H-NMR spectrum of FIG. 1(d). The $^{19}$F-NMR spectrum of FIG. 2(d) shows three fluorine-substituted vinyl peaks, which proves a very pure single material. From the $^1$H-NMR and $^{19}$F-NMR spectrum, preparation of [3-[(trifluorovinyl)oxy]phenyl]triethoxysilane (PFCBSI) was confirmed.

Example 2

Preparation of Sol-Gel Hybrid Polymer Using PFCB

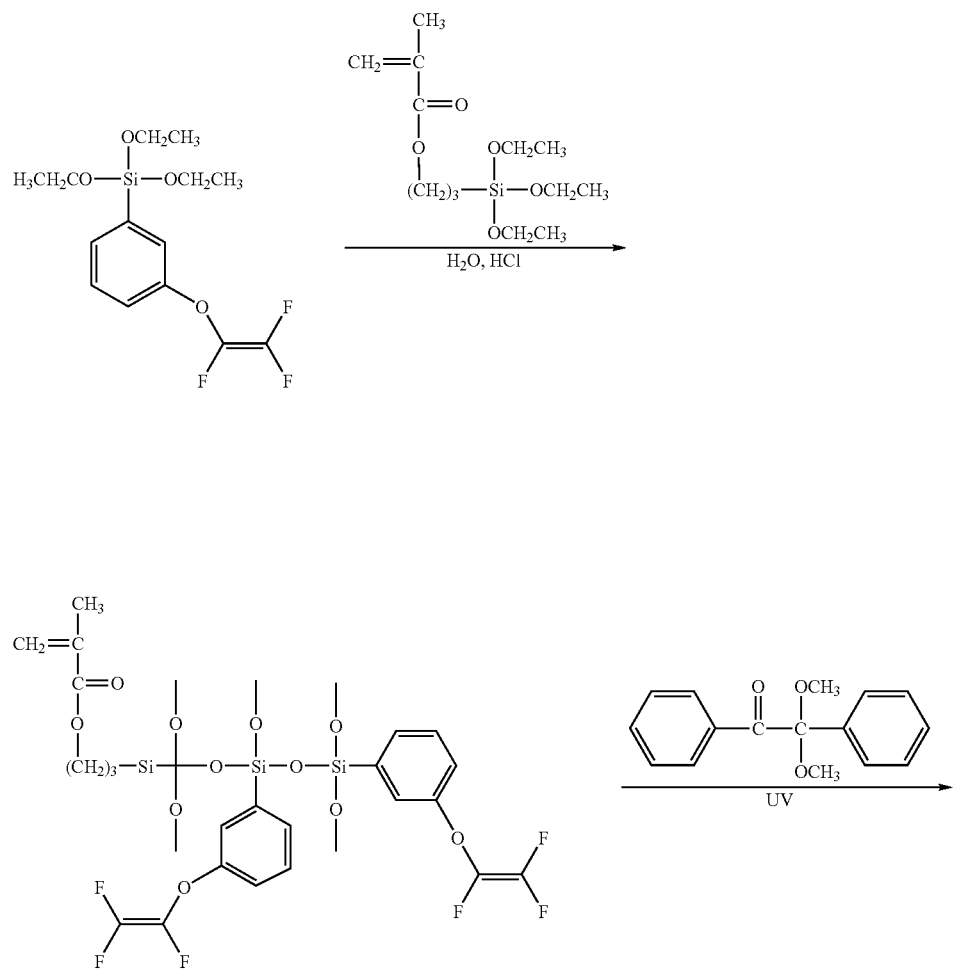

-continued

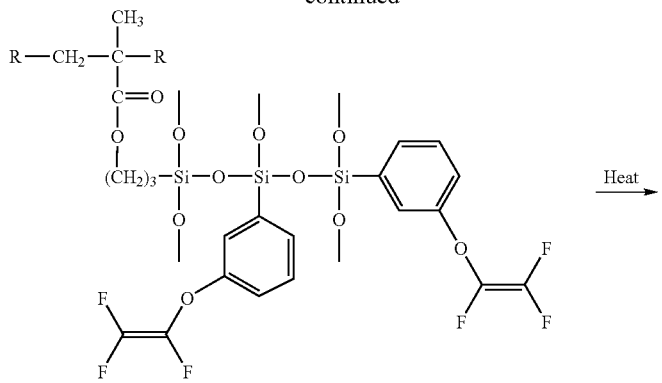

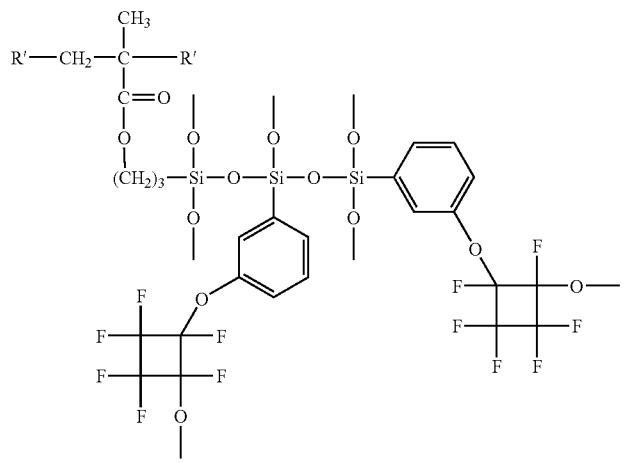

(1) Preparation of Sol-Gel Monomer 1 mol of 3-[(trifluorovinyl)oxy]phenyl]triethoxysilane (PFCBSI) prepared in Example 1, 2 mol of water, 2 mol of HCl and 9 mol of 3-(triethoxysilyl)propylmethacrylate (MSI) were put in a 2-bulb flask purged with nitrogen and maintained at room temperature. Then, a sol-gel monomer containing a trifluorovinylether (—OC$_2$F$_3$) group was prepared from sol-gel reaction.

Figure 3:
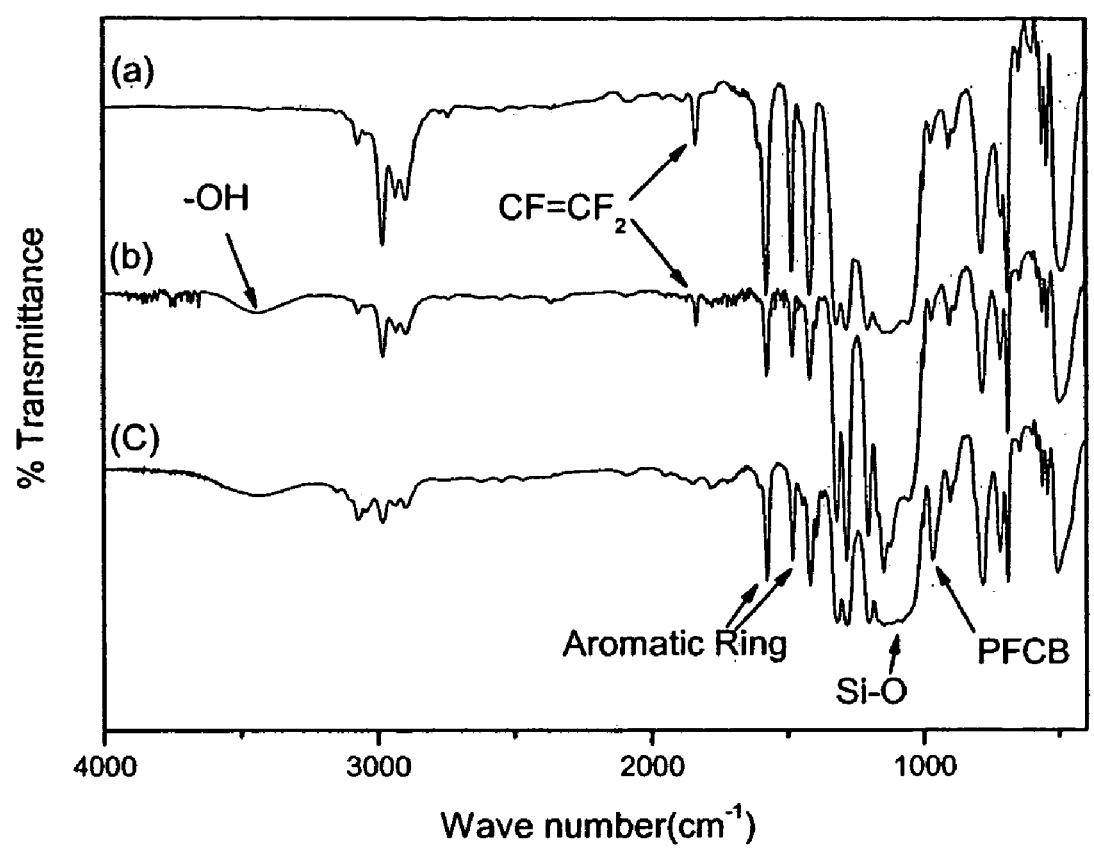
FIG. 3 shows FT-IR spectrums (a) before sol-gel reaction, (b) after sol-gel reaction and (c) after post-baking.

The FT-IR spectrums of FIG. 3 compare before (a) and after (b) the sol-gel reaction. Before the sol-gel reaction (a), there were aliphatic C—H bonding and aromatic C—H bonding peaks around 2,840 cm$^{-1}$ and 3,070 cm$^{-1}$, respectively. After the sol-gel reaction (b), intensity of the peak around 2,840 cm$^{-1}$ has lowered, a hydroxy (—OH) peak has appeared at 3,440 cm$^{-1}$ and a broad Si—O—Si peak has appeared centered at 1,098 cm$^{-1}$, which confirms the sol-gel reaction.

The sol-gel reaction is known to be dependent on the proportion of acid and water. Effect of water content on the molecular weight and its distribution was confirmed by gel permeation chromatography. The result is shown in Table 1 below. In the present invention, it was confirmed that the water content does not affect the solubility a lot.

TABLE 1

Molecular weight and molecular weight distribution of sol-gel monomer

| Water content | Number-average molecular weight (Mn) | Weight-average molecular weight (Mw) | Molecular weight distribution (MWD) |
|---|---|---|---|
| 2 molar equivalents | 1,647 | 2,147 | 1.303 |
| 2.5 molar equivalents | 2,030 | 2,227 | 1.097 |
| 3 molar equivalents | 1,571 | 2,056 | 1.308 |
| 3.5 molar equivalents | 1,622 | 2,154 | 1.327 |
| 4 molar equivalents | 1,595 | 2,280 | 1.429 |

(2) Preparation of Sol-Gel Hybrid Polymer 2,2-dimethoxy-2-phenylacetophenone was added to the prepared sol-gel monomer as photoinitiator. Radical polymerization was performed by illuminating UV ray. Then, the temperature was increased 160° C. to obtain a sol-gel hybrid polymer.

From the FT-IR spectrum of FIG. 3(c), it can be seen that trifluorovinyl double bonding (FC=CF$_2$) absorption peak at 1833 cm$^{-1}$ has disappeared and C—F absorption peak of PFCB at 965 cm$^{-1}$ has appeared after post-baking, which confirms preparation of a sol-gel hybrid polymer containing PFCB.

Test Example 1

Preparation of Sol-Gel Film

Figure 4:
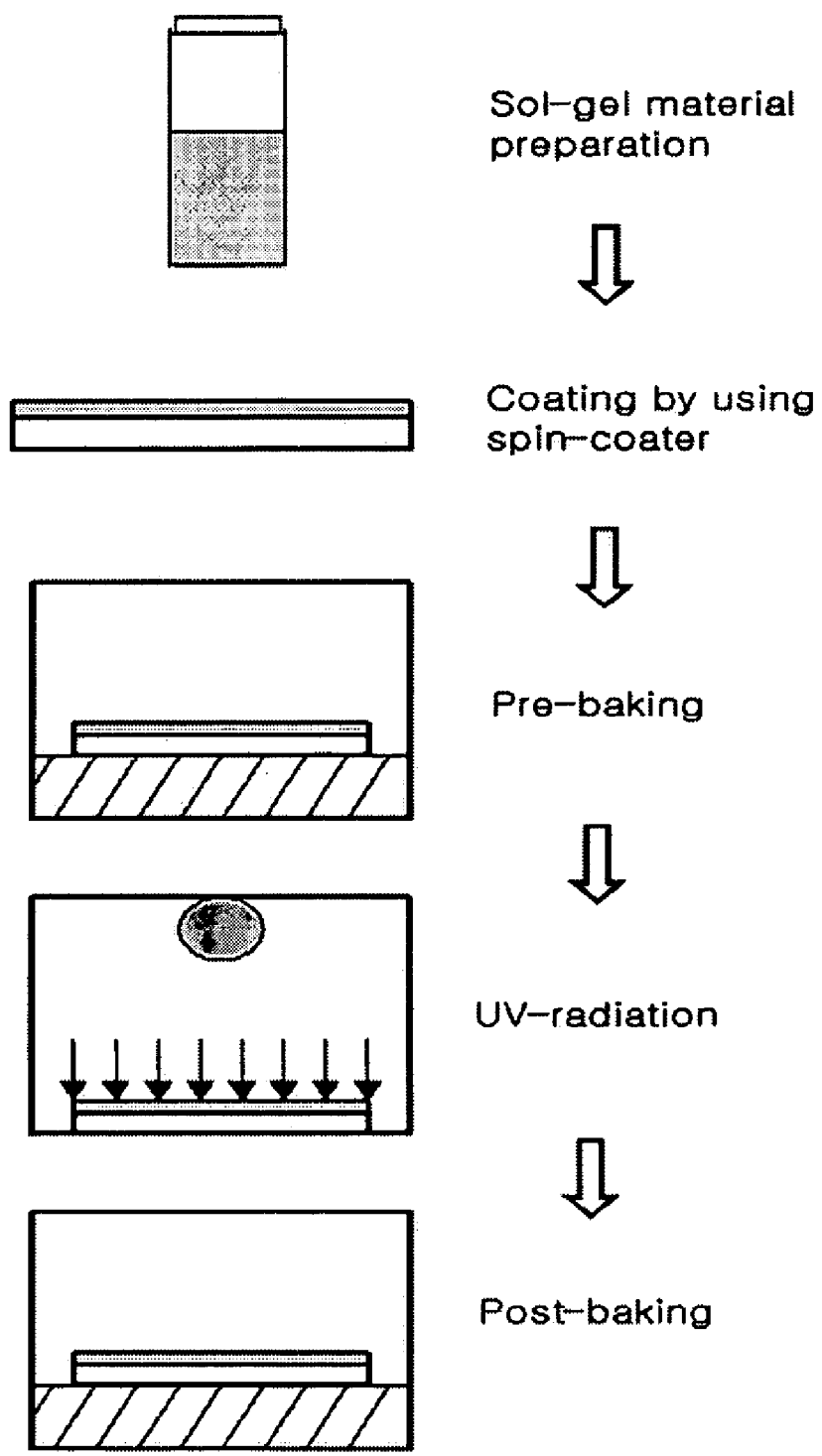
FIG. 4 is a schematic diagram showing the process of preparing film using sol-gel hybrid polymer.

Sol-gel film was prepared according to FIG. 4 using the reaction of Example 2.

Figure 5:
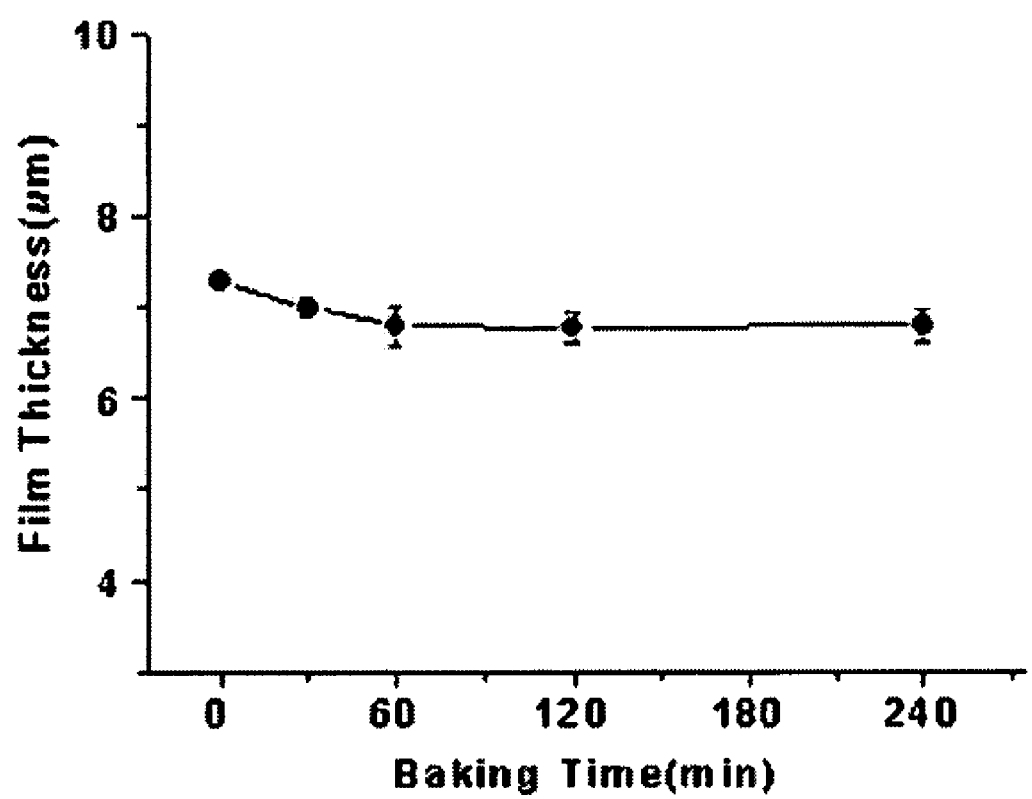
FIG. 5 is a graph that shows the relationship of baking time and film thickness.
Figure 6:
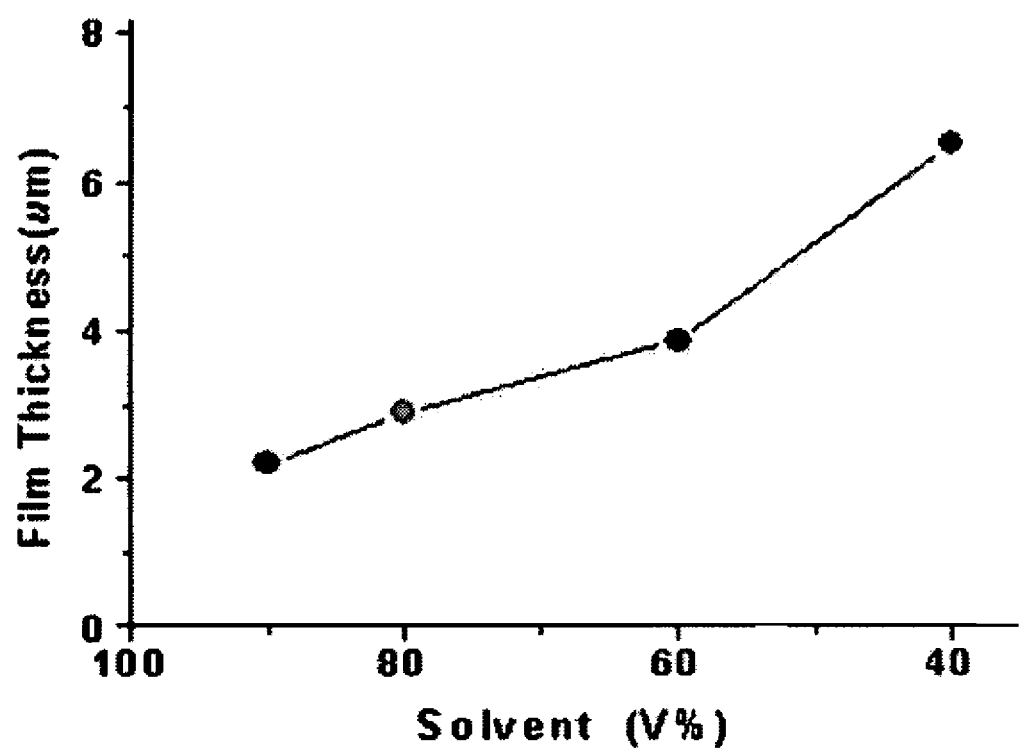
FIG. 6 is a graph that shows the relationship of solvent volume and film thickness during preparation of film using sol-gel hybrid polymer.

Sol-gel solutions prepared in Example 2 using the monomers prepared in Example 1 gave different film shapes depending on the contents of water, acid and solvent. During the film preparation, ethyl alcohol, benzene, cyclohexane and tetrachloroethane were used as solvent, and sulfuric acid, hydrochloric acid and nitric acid was used as acid. The most important factors in sol-gel film preparation are film thickness and transparency. If the sol-gel hybrid polymer is directly dropped on a silicon wafer, the film may crack. To prevent such cracking, a crosslinking agent such as 3-(triethoxysilyl)propylmethacrylate (MSI), was used during the sol-gel monomer preparation. The solvent concentration was controlled to 40 to 45% to optimize the film thickness. As seen in FIG. 5, the sol-gel film thickness decreased as the baking time increased because the solvent, water and ethanol evaporated at high temperature. The PFCBSI monomer prepared in Example 1 offered a uniform film without cracking using tetrachloroethane solvent. When alcohol solvent was used all films cracked during baking, and when cyclohexane was used white precipitate was formed during preparation of the sol-gel solution. When excess acid or water was added, precipitate was formed during preparation of the sol-gel solution or the film cracked. The solvent also affected the film thickness. As seen in FIG. 6, the film thickness decreased as the solvent volume increased. After baking, the film was insoluble in solvents such as THF, acetone, hexane and alcohol, which confirms good crosslinkage.

Test Example 2

Thermal Properties of Sol-Gel Film

The most fundamental requirement of optical waveguide device manufacturing is heat stability. In general, sol-gel polymers are known to have poor heat stability.

Figure 7:
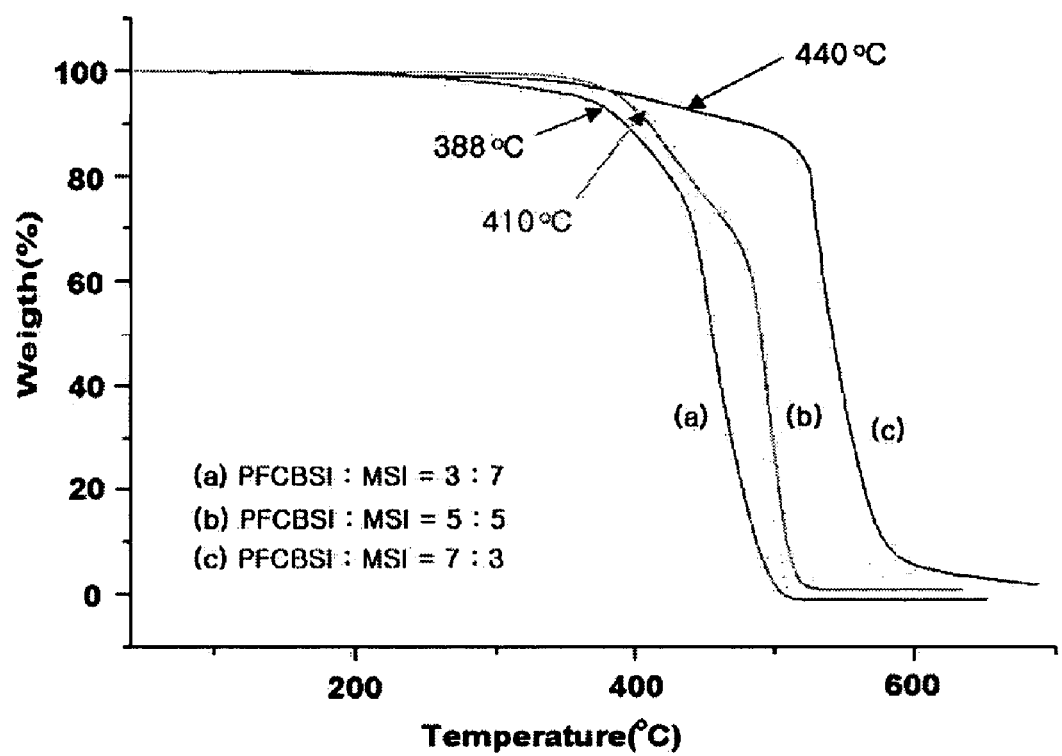
FIG. 7 shows TGA graphs for different molar ratios of PFCBSI and MSI.
Figure 8:
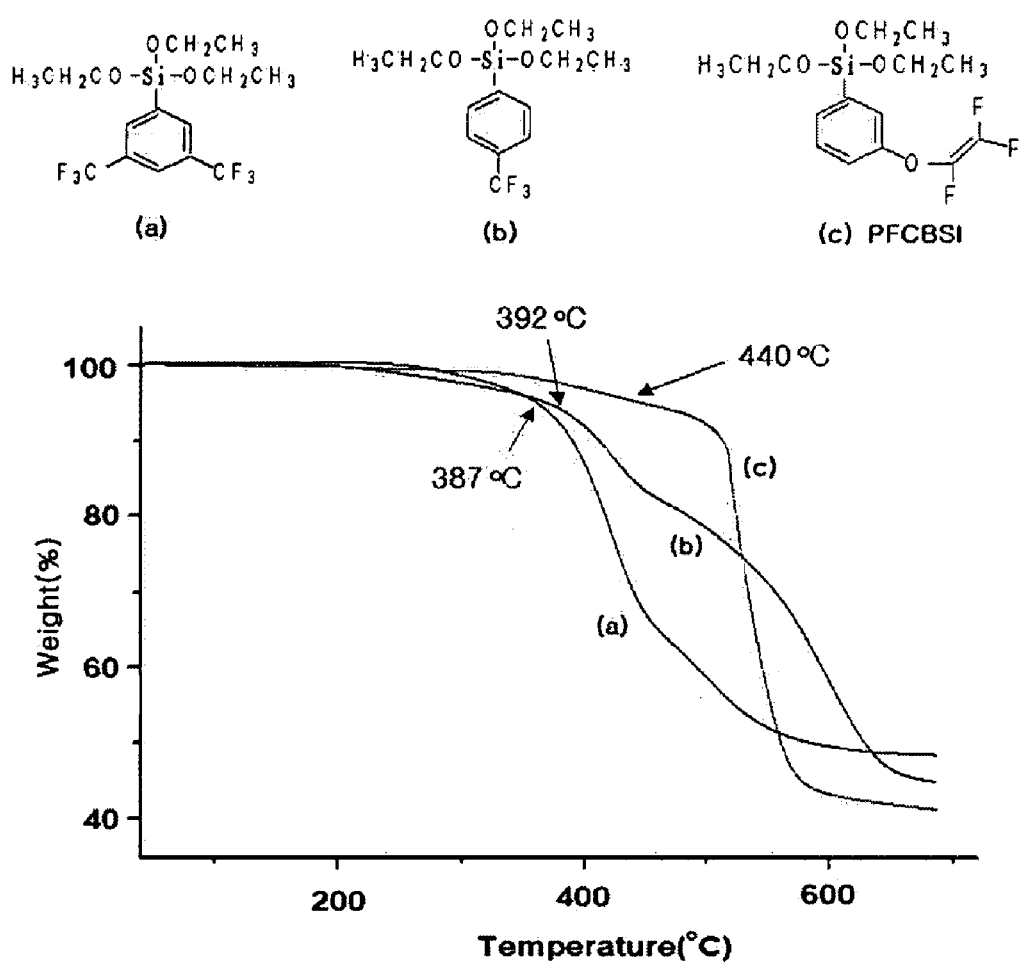
FIG. 8 shows TGA graphs of different monomer containing PFCBSI, fluorine and silicon.

However, the sol-gel polymer of the present invention, which contains 3-(triethoxysilyl)propylmethacrylate (MSI) and trifluorovinylether (—OC$_2$F$_3$) groups, has hydrogen-substituted double bonding and fluorine-substituted double bonding that may form crosslinkage. Therefore, the sol-gel polymer of the present invention has good heat stability. Especially, as seen in the TGA graph of FIG. 7, the heat stability of the sol-gel polymer could be improved by increasing the content of the 3-[(trifluorovinyl)oxy]phenyl]triethoxysilane (PFCBSI) monomer in preparing the sol-gel monomer represented by Chemical Formula 5. Heat stabilities of the sol-gel monomer of the present invention and the conventional silicon-containing monomers are compared in FIG. 8. The sol-gel monomer of the present invention (c) has better heat stability than the conventional silicon-containing monomers.

Test Example 3

Optical Properties of Sol-Gel Hybrid Polymer

Figure 9:
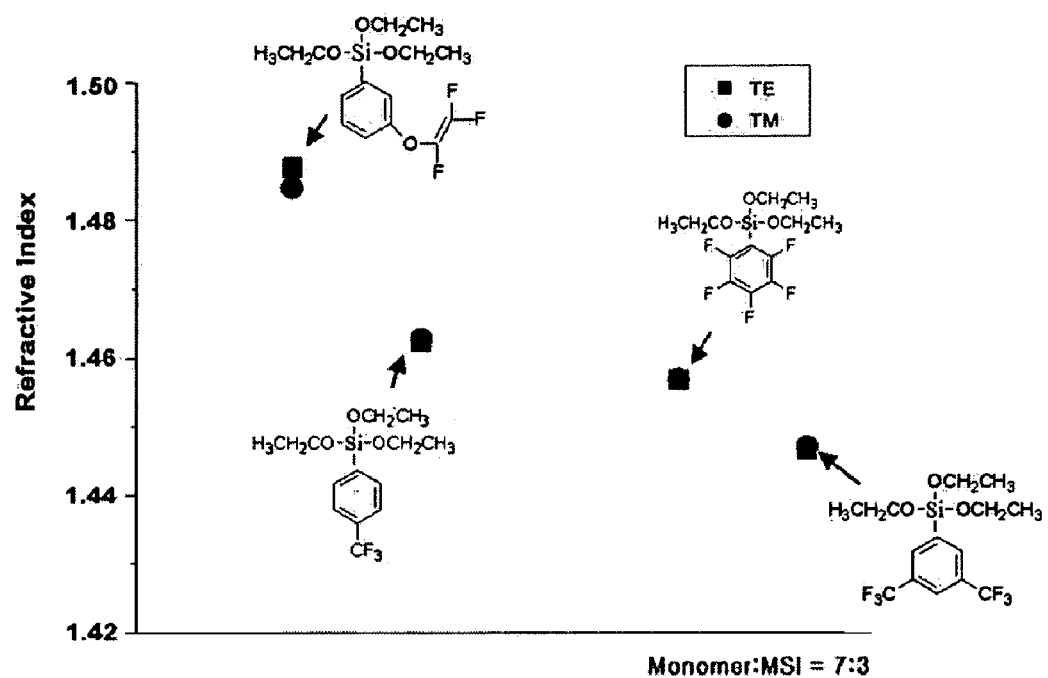
FIG. 9 shows refractive indices of different monomer containing PFCBSI, fluorine and silicon.

The ability to control refractive index is a very important factor of optical waveguides. In general, the refractive index decreases as the fluorine content increases. In the present invention, contents of the PFCBSI monomer and the MSI monomer are controlled to obtain ideal refractive index. In Example 2, the molar ratio of PFCBSI and MSI was set at 7:3 during preparation of the sol-gel polymer. FIG. 9 shows refractive indices at TE and TM modes along with refractive indices of other fluorine- and silicon-containing monomers.

Figure 10:
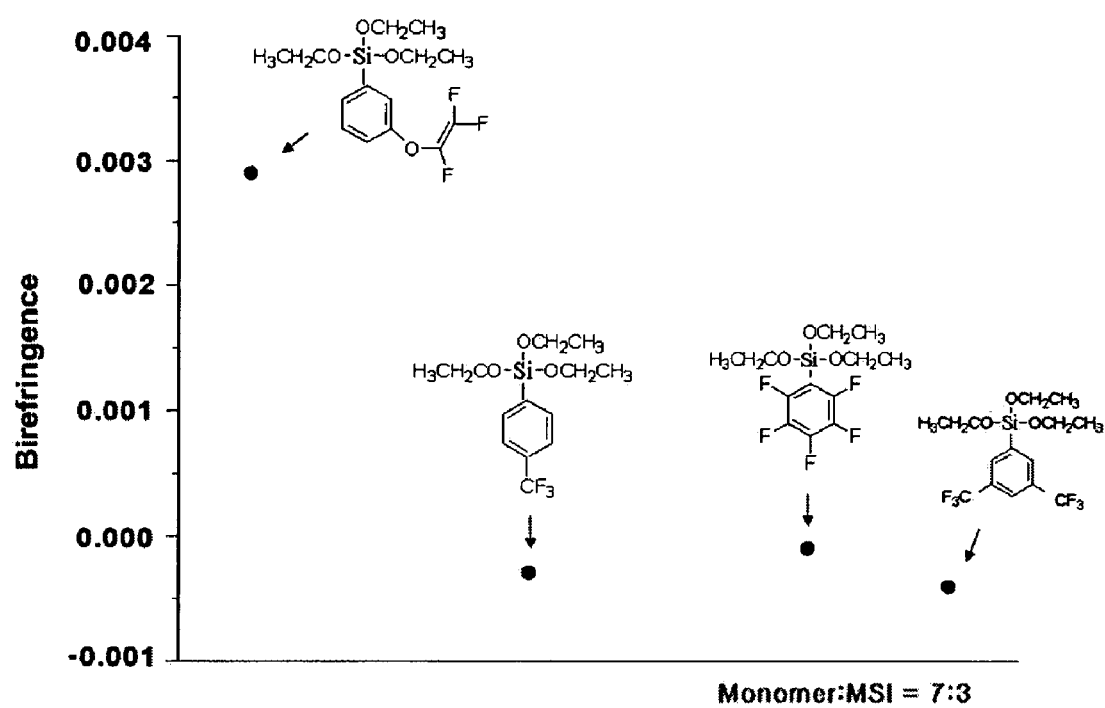
FIG. 10 shows birefringences of different monomer containing PFCBSI, fluorine and silicon.

A polymer should have low birefringence to be used for optical waveguide devices. In general, silicon-containing sol-gel films are known to have low birefringence. Usually, polymer materials have a birefringence of $10^{-3}$ order. As seen in FIG. 10, the sol-gel hybrid polymer of the present invention showed superior birefringence.

Figure 11:
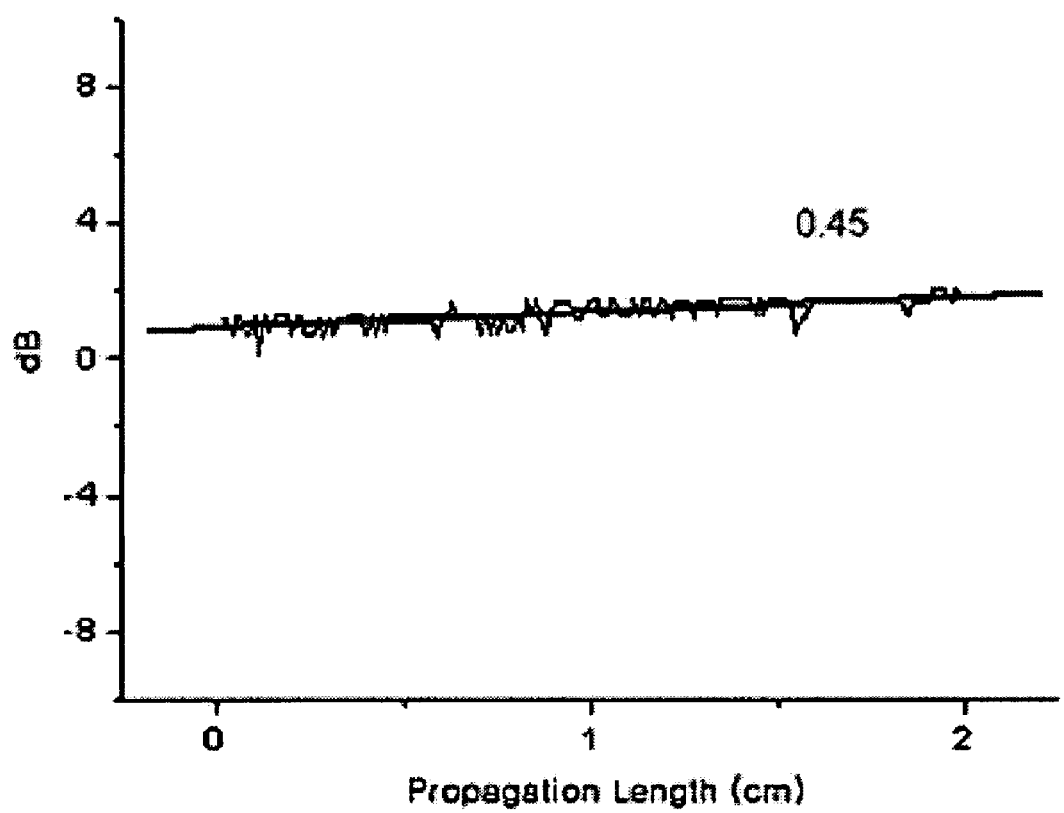
FIG. 11 shows optical waveguide loss for 1.55 μm optical communication band when PFCBSI:MSI=5:5.

Low optical waveguide loss at 1.3 μm or 1.55 μm is very important for polymer materials for optical waveguide devices. Optical loss of optical waveguides is caused by inherent light absorption, inherent optical scattering, dusts, inaccuracies related with manufacturing processes and impurities. The most important factor among them is the inherent light absorption of the polymer. Typically, optical waveguide loss results from secondary and tertiary harmonic vibrations due to the C—H bonding. This problem can be solved by substituting the C—H bonding with deuterium (C-D) or fluorine (C—F) to increase reduced mass, thereby shifting the harmonic vibrations to longer wavelength and minimizing absorption in the optical communication wavelength region. However, in the present invention, because the C—H bonding is decreased by the sol-gel reaction, the main bonding is formed by silicon (Si) and is substituted by fluorine, the optical waveguide loss at 1.55 μm, which corresponds to the optical communication wavelength region, is low, as seen in the FIG. 11.

As described above, the novel monomer of the present invention contains trifluorovinylether (—OC$_2$F$_3$) and silicon (Si), so that it offers a sol-gel hybrid polymer having superior heat resistance, heat stability, mechanical properties and adhesivity. The novel sol-gel hybrid polymer prepared by using the monomer of the present invention is amorphous because it contains perfluorocyclobutane (PFCB), has birefringence appropriate for optical waveguides, has heat stability comparable to that of the conventional fluorine-containing polymers and has superior adhesivity. Therefore, it can contribute to the development of electronics industry, used for optical waveguide devices.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A hybrid polymer represented by the following Chemical Formula 2:

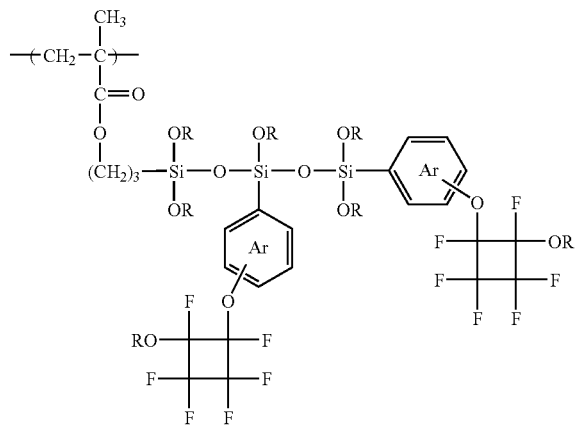

(2)

wherein
R is a hydrogen atom or a $C_1$ to $C_6$ alkyl group;

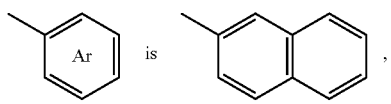

Ar is

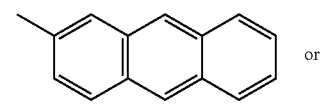

or

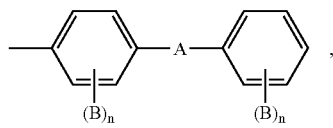

wherein trifluorovinylether ($-OC_2F_3$) group can be substituted at o-, m- or p-position;
-A- is a bond

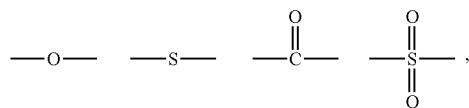

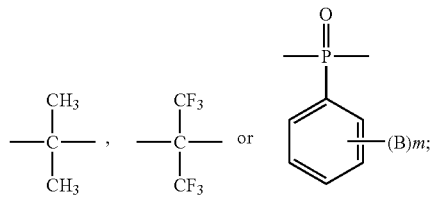

B is a hydrogen atom, a fluorine atom, a $C_1$ to $C_6$ alkyl group or a $C_1$ to $C_6$ fluoroalkyl group;
n and m are respectively the number of substituents B, wherein n is an integer of 1 to 4 and m is an integer of 1 to 5.

2. A method of preparing a hybrid polymer represented by Chemical Formula 2 below comprising the steps of:

preparing a monomer containing a trifluorovinylether ($-OC_2F_3$) group from reaction of a siloxane monomer represented by Chemical Formula 1 below in the presence of a crosslinking agent, water and hydrochloric acid; and polymerizing the resultant monomer by illuminating UV ray:

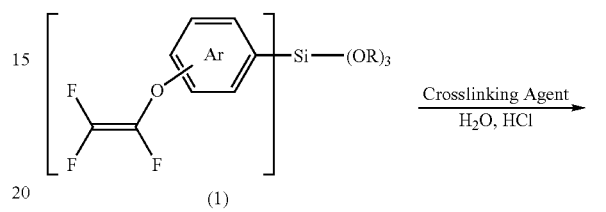

(1)

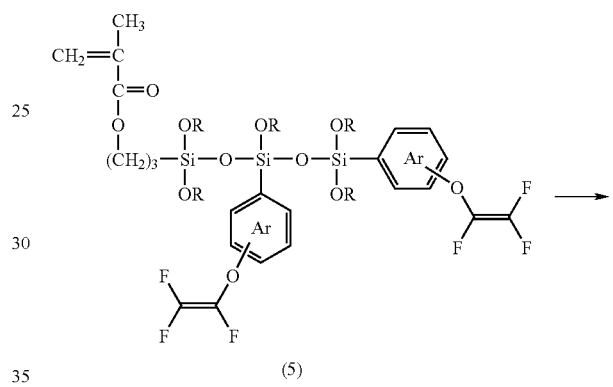

(5)

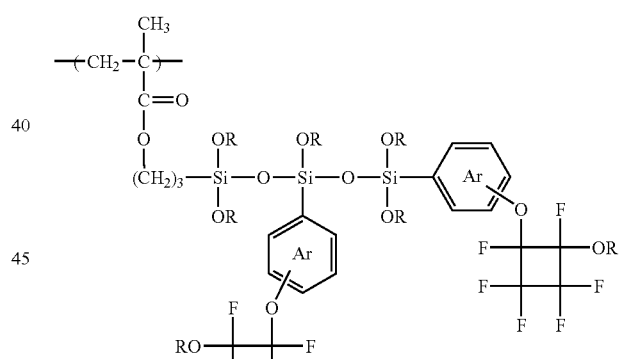

(2)

wherein
R is a hydrogen atom or a $C_1$ to $C_6$ alkyl group;

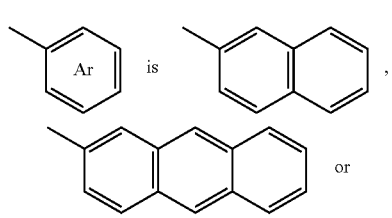

or

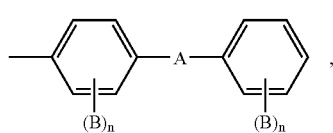

wherein trifluorovinylether (—OC$_2$F$_3$) group can be substituted at o-, m- or p-position;

-A- is a bond,

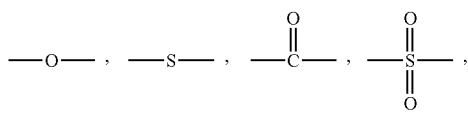

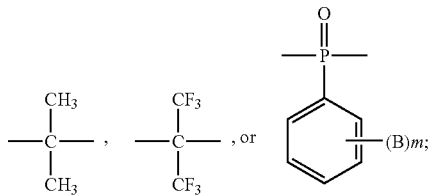

B is a hydrogen atom, a fluorine atom, a C$_1$ to C$_6$ alkyl group or a C$_1$ to C$_6$ fluoroalkyl group;

n and m are respectively the number of substituents B, wherein n is an integer of 1 to 4 and m is an integer of 1 to 5.

3. The method of preparing a hybrid polymer according to claim 2, wherein the molar ratio of said siloxane monomer and said crosslinking agent ranges from 3:7 to 7:3.

4. A film prepared by said hybrid polymer of claim 1.

* * * * *